US011122992B2

(12) United States Patent
Govari et al.

(10) Patent No.: US 11,122,992 B2
(45) Date of Patent: Sep. 21, 2021

(54) DETERMINING A LOCATION AND AN ORIENTATION OF A MAGNETIC FIELD SENSOR

(71) Applicant: Biosense Webster (Israel) Ltd., Yokneam (IL)

(72) Inventors: Assaf Govari, Haifa (IL); Vadim Gliner, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 442 days.

(21) Appl. No.: 16/103,176

(22) Filed: Aug. 14, 2018

(65) Prior Publication Data

US 2020/0054244 A1 Feb. 20, 2020

(51) Int. Cl.
*A61B 5/055* (2006.01)
*A61B 5/06* (2006.01)
(Continued)

(52) U.S. Cl.
CPC .............. *A61B 5/066* (2013.01); *A61B 5/055* (2013.01); *A61B 5/063* (2013.01); *A61B 18/1492* (2013.01); *A61M 2025/0166* (2013.01)

(58) Field of Classification Search
CPC ......... A61B 5/066; A61B 5/055; A61B 5/063; A61B 18/1492; A61B 5/0044;
(Continued)

(56) References Cited

U.S. PATENT DOCUMENTS 5,391,199 A * 2/1995 Ben-Haim ........... A61B 5/6843
607/122
5,443,489 A 8/1995 Ben-Haim
(Continued)

FOREIGN PATENT DOCUMENTS

EP 0722290 A1 7/1997
EP 1126787 A1 8/2001
WO 2016181316 A1 11/2016

OTHER PUBLICATIONS

Pujol et al: "Preliminary Results of Nonfluoroscopy-based 3D Navigation for Neurointerventional Procedures", Journal of Vascular and Interventional Radiology, Elsevier, Amsterdam, NL, vol. 18, No. 2, Feb. 21, 2007 (Feb. 21, 2007), pp. 289-298.
(Continued)

*Primary Examiner* — Bill Thomson
*Assistant Examiner* — Zainab Mohammed Aldarraji
(74) *Attorney, Agent, or Firm* — Notaro, Michalos & Zaccaria P.C.

(57) ABSTRACT

A method, including receiving from a sensor affixed to a probe, signals output by the sensor in response to a calibrated magnetic field, and estimating, using calibration data, location coordinates of the sensor. Using the calibration data and the estimated location, an estimated vector including orientation coordinates is computed, and updated orientation coordinates that best fit the received signals to the estimated vector are computed for the estimated location. Based on the updated orientation, updated location coordinates that best fit the received signals to the estimated vector are computed. The steps of computing the vector, computing the orientation, and computing the location and monitoring changes in the updated location are repeated until the changes are linear. Upon the changes being linear, a final location of the sensor is computed using a linear projection from the updated
(Continued)

location, and a position of the probe is presented based on the final location.

17 Claims, 4 Drawing Sheets

(51) Int. Cl.
*A61B 18/14* (2006.01)
*A61M 25/01* (2006.01)

(58) Field of Classification Search
CPC ..... A61B 5/743; A61B 5/1071; A61B 5/0422; A61B 5/062; A61B 5/1495; A61B 18/12; A61B 34/20; A61B 2018/00351; A61B 2018/00595; A61B 2018/00577; A61B 2034/2051; A61M 2025/0166
See application file for complete search history.

(56) References Cited

U.S. PATENT DOCUMENTS

| | | | | |
|---|---|---|---|---|
| 5,558,091 A * | 9/1996 | Acker | .................... | A61B 5/062 600/424 |
| 6,172,499 B1 | 1/2001 | Ashe | | |
| 6,177,792 B1 * | 1/2001 | Govari | .................... | G01B 7/004 324/207.12 |
| 6,263,230 B1 * | 7/2001 | Haynor | .................. | A61B 5/062 128/899 |
| 6,522,907 B1 * | 2/2003 | Bladen | ..................... | A61B 5/06 128/899 |
| 6,690,963 B2 * | 2/2004 | Ben-Haim | ............. | A61B 5/145 600/424 |
| 6,788,967 B2 | 9/2004 | Ben-Haim et al. | | |
| 2010/0280353 A1 * | 11/2010 | Roth | ..................... | G01R 33/028 600/410 |
| 2012/0150022 A1 * | 6/2012 | Bar-Tai | ................. | A61B 5/063 600/424 |
| 2013/0066193 A1 * | 3/2013 | Olson | .................... | A61B 5/063 600/424 |
| 2014/0104059 A1 * | 4/2014 | Tran | ...................... | A61B 5/1116 340/539.12 |
| 2014/0155098 A1 | 6/2014 | Markham et al. | | |
| 2015/0087965 A1 * | 3/2015 | Tokuda | ................. | G06T 3/0068 600/414 |
| 2017/0115364 A1 * | 4/2017 | Efrat | ..................... | G01R 33/10 |

OTHER PUBLICATIONS

Extended European search report for corresponding European patent application No. EP 19191531.3, dated Oct. 30, 2019.

* cited by examiner

DETERMINING A LOCATION AND AN ORIENTATION OF A MAGNETIC FIELD SENSOR

FIELD OF THE INVENTION

The present invention relates generally to medical imaging, and specifically to determining a location and an orientation of a distal end of a medical probe positioned in a body cavity.

BACKGROUND OF THE INVENTION

A wide range of medical procedures involve placing objects, such as sensors, tubes, catheters, dispensing devices, and implants, within the body. Real-time imaging methods are often used to assist doctors in visualizing the object and its surroundings during these procedures. In most situations, however, real-time three-dimensional imaging is not possible or desirable. Instead, systems for obtaining real-time spatial coordinates of the internal object are often utilized.

WIPO Patent Application WO/2016/181316 to Schwartz et al. describes a method of tracking an intra-body catheter. The method includes correcting physically tracked location coordinates with simulated coordinates that were generated according to a simulation of a simulated catheter within a simulation of the body of the patient.

U.S. Patent Application 2014/0155098 to Markham et al. describes a system for providing location information of a mobile device positioned among units that are spread apart at a distance. The mobile device is configured to determine its location based on information extracted from a field emitted from a given local unit.

U.S. Patent Application 2014/0104059 to Tran describes a method of automatically requesting assistance for a patient by verbally communicating with a user through a base unit. The method includes using a plurality of wireless nodes to transmit position and triangulating with the mobile node to determine the patient's position.

The description above is presented as a general overview of related art in this field and should not be construed as an admission that any of the information it contains constitutes prior art against the present patent application.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

There is provided, in accordance with an embodiment of the present invention a method, including receiving by a processor, from a magnetic field sensor affixed to a probe, signals output by the sensor in response to a calibrated magnetic field in a vicinity of the probe, estimating, by the processor, using calibration data with respect to the magnetic field, location coordinates of the magnetic field sensor, computing by the processor, using the calibration data and the estimated location coordinates, an estimated magnetic field vector including orientation coordinates, computing by the processor, for the estimated location coordinates, updated orientation coordinates that best fit the received signals to the estimated magnetic field vector, computing by the processor, based on the updated orientation coordinates, updated location coordinates that best fit the received signals to the estimated magnetic field vector, repeating over multiple iterations the steps of computing the estimated magnetic field vector, computing the updated orientation coordinates, and computing the updated location coordinates and monitoring changes in the updated location coordinates over the iterations until the changes over a succession of the iterations meet a predefined linearity criterion, upon detecting that the changes have met the linearity criterion, terminating the iterations and computing final location coordinates of the magnetic field sensor by a linear projection from the updated location coordinates, and presenting, on a display, a position of the probe based on the final location coordinates and the updated orientation coordinates.

In some embodiments the method may include computing by the processor, using the calibration data and the final location coordinates, final magnetic field vector including orientation coordinates, computing by the processor, for the final location coordinates, final orientation coordinates that best fit the received signals to the final magnetic field vector, and presenting, on the display, the position of the probe based on the final location coordinates and the final orientation coordinates.

In one embodiment, the probe includes an intracardiac catheter inserted into a chamber of a heart. In additional embodiments, the orientation coordinates include Euler angles including a roll angle, a pitch angle and a yaw angle. In further embodiments, the location coordinates include three-dimensional coordinates on multiple axes in a coordinate system.

In supplemental embodiments, the multiple iterations include a first iteration followed successively by a second iteration followed successively by a third iteration, and wherein the linearity criterion includes detecting that a distance between the updated location coordinates computed during the first iteration and the updated location coordinates computed during the second iteration is in accordance with a distance between the updated location coordinates computed during the second iteration and the updated location coordinates computed during the third iteration.

In some embodiments, the multiple iterations include a first iteration followed successively by a second iteration followed successively by a third iteration, and wherein the linearity criterion includes detecting that a slope from the updated location coordinates computed during the first iteration to the updates location coordinates computed during the second iteration is in accordance with a slope from the updated location coordinates computed during the second iteration to the updates location coordinates computed during the third iteration.

There is also provided, in accordance with an embodiment of the present invention an apparatus, including a medical probe configured to be inserted into a body cavity, a magnetic field sensor affixed to the probe, a display, and a processor configured to receive, from the magnetic field sensor affixed to the probe, signals output by the sensor in response to a calibrated magnetic field in a vicinity of the probe, to estimate, using calibration data with respect to the magnetic field, location coordinates of the magnetic field sensor, to compute, using the calibration data and the estimated location coordinates, an estimated magnetic field vector including orientation coordinates, to compute, for the estimated location coordinates, updated orientation coordinates that best fit the received signals to the estimated magnetic field vector, to compute, based on the updated orientation coordinates, updated location coordinates that best fit the received signals to the estimated magnetic field vector, to repeat over multiple iterations the steps of computing the estimated magnetic field vector, computing the updated orientation coordinates, and computing the updated location coordinates and monitoring changes in the updated location coordinates over the iterations until the changes over a succession of the iterations meet a predefined linearity criterion, upon detecting that the changes have met the linearity criterion, to terminate the iterations and to compute final location coordinates of the magnetic field sensor by a linear projection from the updated location coordinates, and to present, on the display, a position of the probe based on the final location coordinates and the updated orientation coordinates.

There is further provided, in accordance with an embodiment of the present invention, a computer software product, operated in conjunction with a probe that is configured for insertion into a body cavity of a patient and includes a magnetic sensor, the product including a non-transitory computer-readable medium, in which program instructions are stored, which instructions, when read by a computer, cause the computer to receive, from the magnetic field sensor affixed to the probe, signals output by the sensor in response to a calibrated magnetic field in a vicinity of the probe, to estimate, using calibration data with respect to the magnetic field, location coordinates of the magnetic field sensor, to compute, using the calibration data and the estimated location coordinates, an estimated magnetic field vector including orientation coordinates, to compute, for the estimated location coordinates, updated orientation coordinates that best fit the received signals to the estimated magnetic field vector, to compute, based on the updated orientation coordinates, updated location coordinates that best fit the received signals to the estimated magnetic field vector, to repeat over multiple iterations the steps of computing the estimated magnetic field vector, computing the updated orientation coordinates, and computing the updated location coordinates and monitoring changes in the updated location coordinates over the iterations until the changes over a succession of the iterations meet a predefined linearity criterion, upon detecting that the changes have met the linearity criterion, to terminate the iterations and to compute final location coordinates of the magnetic field sensor by a linear projection from the updated location coordinates, and to present, on a display, a position of the probe based on the final location coordinates and the updated orientation coordinates.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

Various medical procedures use an invasive medical probe such as a catheter that is inserted into a patient's body. During the medical procedure, the position of a distal end of the catheter is typically found by a process of iteration, since the position comprises a location and an orientation, which are both initially unknown.

Embodiments of the present invention provide methods and systems for reducing the number of iterations required to estimate location and orientation coordinates of the distal end of the catheter. As described hereinbelow, signals from a magnetic field sensor affixed to a probe are received that were output by the sensor in response to a calibrated magnetic field in a vicinity of the probe. Using calibration data with respect to the magnetic field, location coordinates of the magnetic field sensor are estimated, and using the calibration data and the estimated location coordinates, an estimated magnetic field vector comprising orientation coordinates is computed. For the estimated location coordinates, updated orientation coordinates are computed that best fit the received signals to the estimated magnetic field vector, and based on the updated orientation coordinates, updated location coordinates are computed that best fit the received signals to the estimated magnetic field vector.

The steps of computing the estimated magnetic field vector, computing the updated orientation coordinates, and computing the updated location coordinates, and changes in the updated location coordinates over the iterations are monitored until the changes over a succession of the iterations meet a predefined linearity criterion. Upon detecting that the changes have met the linearity criterion, the iterations are terminated, and final location coordinates of the magnetic field sensor are computed by a linear projection from the updated location coordinates. Finally, a position of the probe based on the final location coordinates and the updated orientation coordinates are presented on a display.

System Description

Figure 1A:
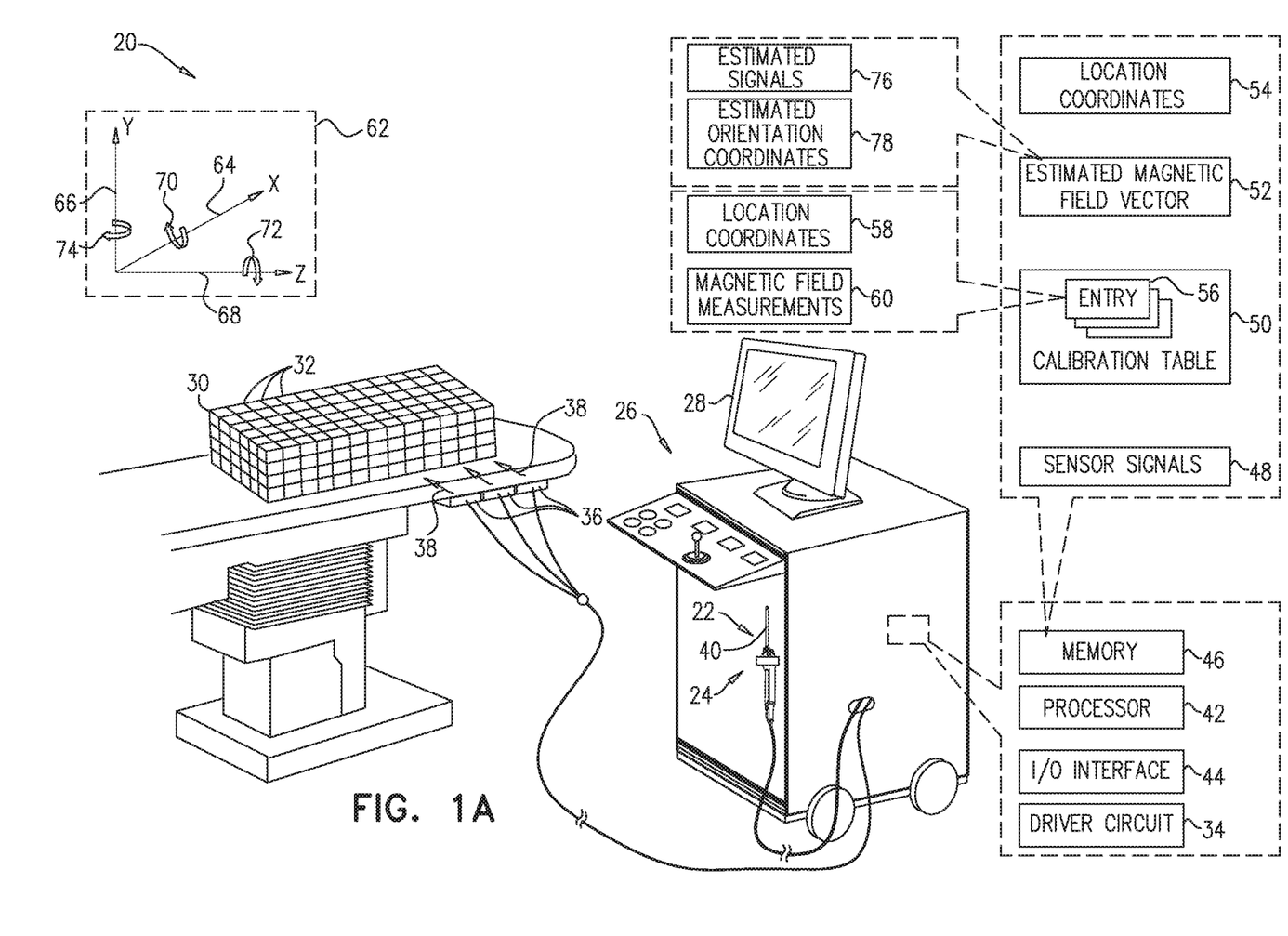
FIGS. 1A and 1B are schematic pictorial illustrations of a medical system configured to estimate a location and an orientation of a distal end of a medical probe inserted into a patient, in accordance with an embodiment of the present invention.
Figure 1B:
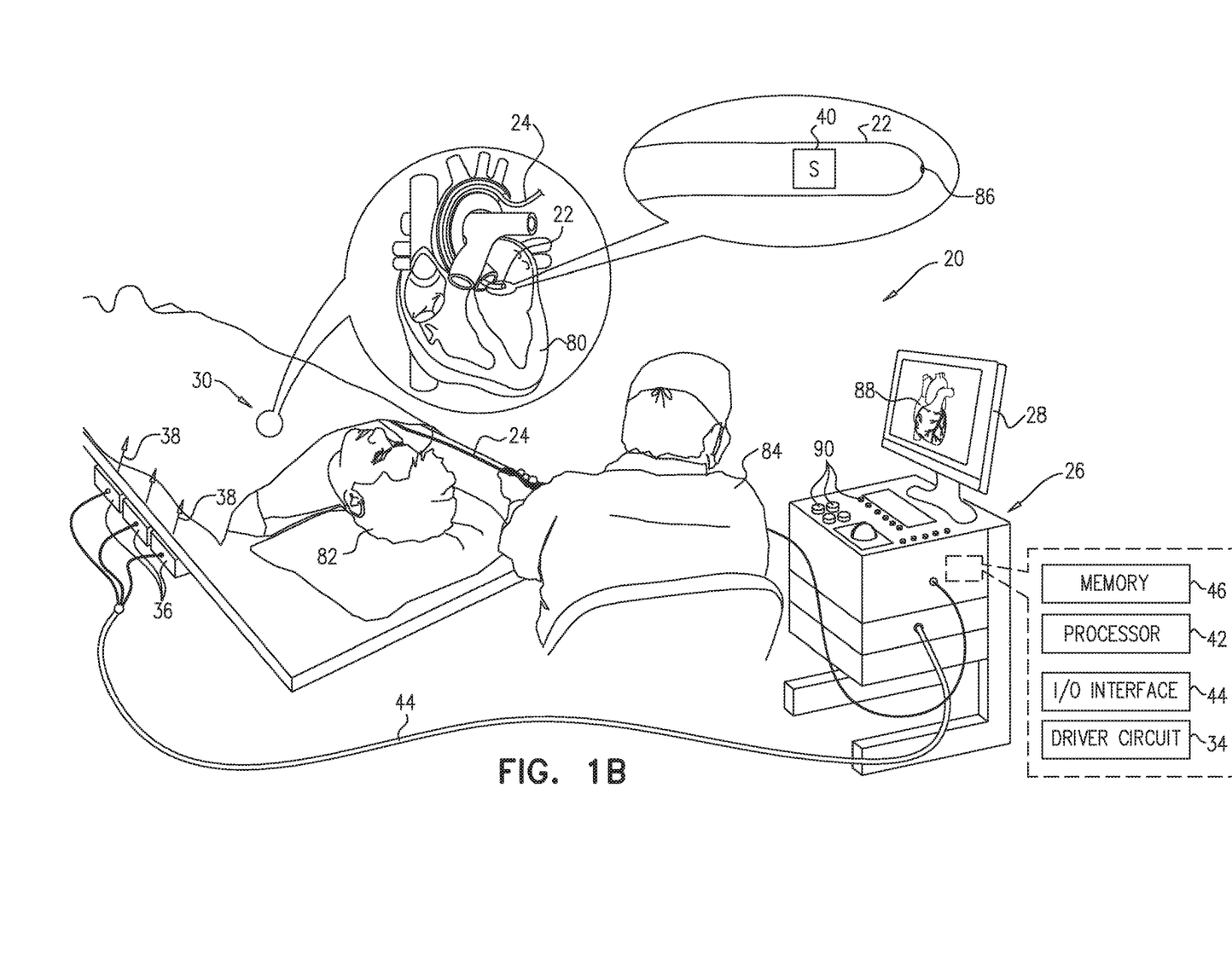

FIGS. 1A and 1B, referred to collectively as FIG. 1, are schematic pictorial illustrations of a medical system 20 configured to track a position (i.e., a location and an orientation) of a distal end 22 of a medical probe 24 during a medical procedure, in accordance with an embodiment of the present invention. Components of medical probe 24 are described in the description referencing FIG. 1B hereinbelow.

Medical system 20 comprises medical probe 24, a control console 26 and a display 28. Display 28 is assumed, by way of example, to comprise a flat panel display such as a liquid crystal display, a light emitting diode display, an organic light-emitting diode display or a plasma display. However, other display devices can also be employed to implement embodiments of the present invention.

In embodiments described herein, medical system 20 uses magnetic position sensing to determine position coordinates that indicate a location and an orientation of distal end 22 inside a predefined working volume 30. In the example shown in FIG. 1A, volume 30 comprises multiple cubic regions 32 having uniform edge lengths (e.g., one centimeter).

To implement magnetic based position sensing, control console 26 comprises a driver circuit 34 which drives field generators 36 to generate magnetic fields 38 within volume 30. Typically, field generators 36 comprise three orthogonally oriented coils, which are placed below the volume at known positions external to volume 30. Distal end 22 comprises a magnetic field sensor 40 (FIG. 1B) that generates signals in response to the magnetic fields.

In addition to driver circuit 34, control console comprises a processor 42, an input/output (I/O) communications interface 44 and a memory 46 that stores sensor signals 48, a calibration table 50, an estimated magnetic field vector 52 and location coordinates 54. Memory 46 may comprise any suitable volatile and/or non-volatile memory, such as random access memory or a hard disk drive. Calibration table 50 comprises multiple entries 56, each of the entries comprising a set of calibration location coordinates 58 and calibration magnetic field measurements 60.

Prior to performing medical procedures, processor 42 can calibrate field generators 36 by storing, to each given entry 56, measurements 60 of magnetic fields 38 at location coordinates 58. Location coordinates 58 comprise a set of coordinates in a three-dimensional coordinate system 62 comprising an X-axis 64, a Y-axis 66 and a Z-axis 68. In addition to axes 64, 66 and 68, coordinate system 62 also comprises a roll angle 70, a pitch angle 72 and a yaw angle 74 that comprise Euler angles and may collectively be referred to as orientation coordinates.

In embodiments of the present invention, each set of location coordinates 58 comprises a set of coordinates within each cubic region 32 (e.g., the coordinates of a center point of each of the cubic regions) at a fixed orientation (i.e., at a specific roll angle 70, a specific pitch angle 72 and a specific yaw angle 74). Upon calibrating field generators 36, magnetic fields 38 may also be referred to as calibrated magnetic fields 38.

Sensor signals 48 comprise signals that processor 42 receives from magnetic field sensor 40 that the magnetic field sensor generates in response to the calibrated magnetic field. Based on the received signals, processor 42 can compute and store magnetic field measurements 60.

Estimated magnetic field vector 52 is derived from estimated signal measurements 76, which provide an estimated size for the vector, and a set of estimated orientation coordinates 78 comprising a given roll angle 70, a given pitch angle 72 and a given yaw angle 74. As described in the description referencing FIG. 2 hereinbelow, processor 42 uses an iterative process to compute location coordinates 54 and orientation coordinates 78 for distal end 22.

In the example shown in FIG. 1B, probe 24 comprises an intracardiac catheter can be used for diagnostic or therapeutic treatment, such as for mapping electrical potentials in a heart 80 of a patient 82. Alternatively, probe 24 may be used, mutatis mutandis, for other therapeutic and/or diagnostic purposes in the heart or in other body organs.

During a medical procedure, a medical professional 84 inserts probe 24 through the vascular system of patient 82 so that distal end 22 of the medical probe enters a chamber of heart 80. As stated supra, console 26 uses magnetic position sensing to determine the location and orientation coordinates (also referred to herein collectively as position coordinates) of distal end 22 inside heart 80. To determine the position coordinates, driver circuit 34 in console 26 drives field generators 36 to generate magnetic fields 38 within the body of patient 82. Field generators are typically placed below the patient's torso at known positions external to patient 82, and generate the magnetic fields in predefined working volume 30 that contains heart 80.

Magnetic field sensor 40 within distal end 22 of probe 24 generates electrical signals in response to these magnetic fields, and as described in the description referencing FIG. 2 hereinbelow, processor 42 processes these signals in order to determine the position coordinates of sensor 40 and distal end 22.

Magnetic field sensor 40 transmits a signal to console 26 in response to magnetic fields 38. Magnetic field sensor 40 may comprise one or more miniature coils, and typically comprises multiple coils oriented along different axes. Although FIG. 1 shows a probe with a single magnetic field sensor, embodiments of the present invention may utilize probes with more than one magnetic field sensor. Magnetic position tracking techniques are described, for example, in U.S. Pat. Nos. 5,391,199, 5,443,489, 6,788,967, 6,690,963, 5,558,091, 6,172,499 6,177,792, whose disclosures are incorporated herein by reference.

In an alternative embodiment, the roles of magnetic field sensor 40 and magnetic field generators 36 may be reversed. In other words, driver circuit 34 may drive a magnetic field generator in distal end 22 to generate one or more magnetic fields 38. The coils in generator 36 may be configured to sense the fields and generate signals indicative of the amplitudes of the components of these magnetic fields. Processor 42 receives and processes these signals in order to determine the position coordinates of distal end 22 within heart 80.

In the configuration presented in FIG. 1B, probe 24 comprises an electrode 86 coupled to distal end 22. In some embodiments, electrode 86 can be configured to measure a certain physiological property (e.g., the local surface electrical potential) at locations inside heart 80.

In operation, I/O communications interface 44 enables control console 26 to transfer signals from magnetic field sensor 40 and electrode 86. Based on signals received from magnetic field sensor 40 and electrode 86, processor 42 can generate a map 88 that shows the position of distal end 22 in the patient's body. During the procedure, processor 42 can present map 88 to medical professional 84 on display 28, and store data representing the map in memory 46. In some embodiments, medical professional 84 can manipulate map 88 using one or more input devices 90. In alternative embodiments, display 28 may comprise a touchscreen that can be configured to accept inputs from medical professional 84, in addition to presenting map 88.

Processor 42 typically comprises a general-purpose computer, with suitable front end and interface circuits for receiving signals from medical probe 24 and controlling the other components of control console 26. Processor 42 may be programmed in software to carry out the functions that are described herein. The software may be downloaded to control console 26 in electronic form, over a network, for example, or it may be provided on non-transitory tangible media, such as optical, magnetic or electronic memory media. Alternatively, some or all of the functions of processor 42 may be carried out by dedicated or programmable digital hardware components.

Location and Orientation Determination

Figure 2:
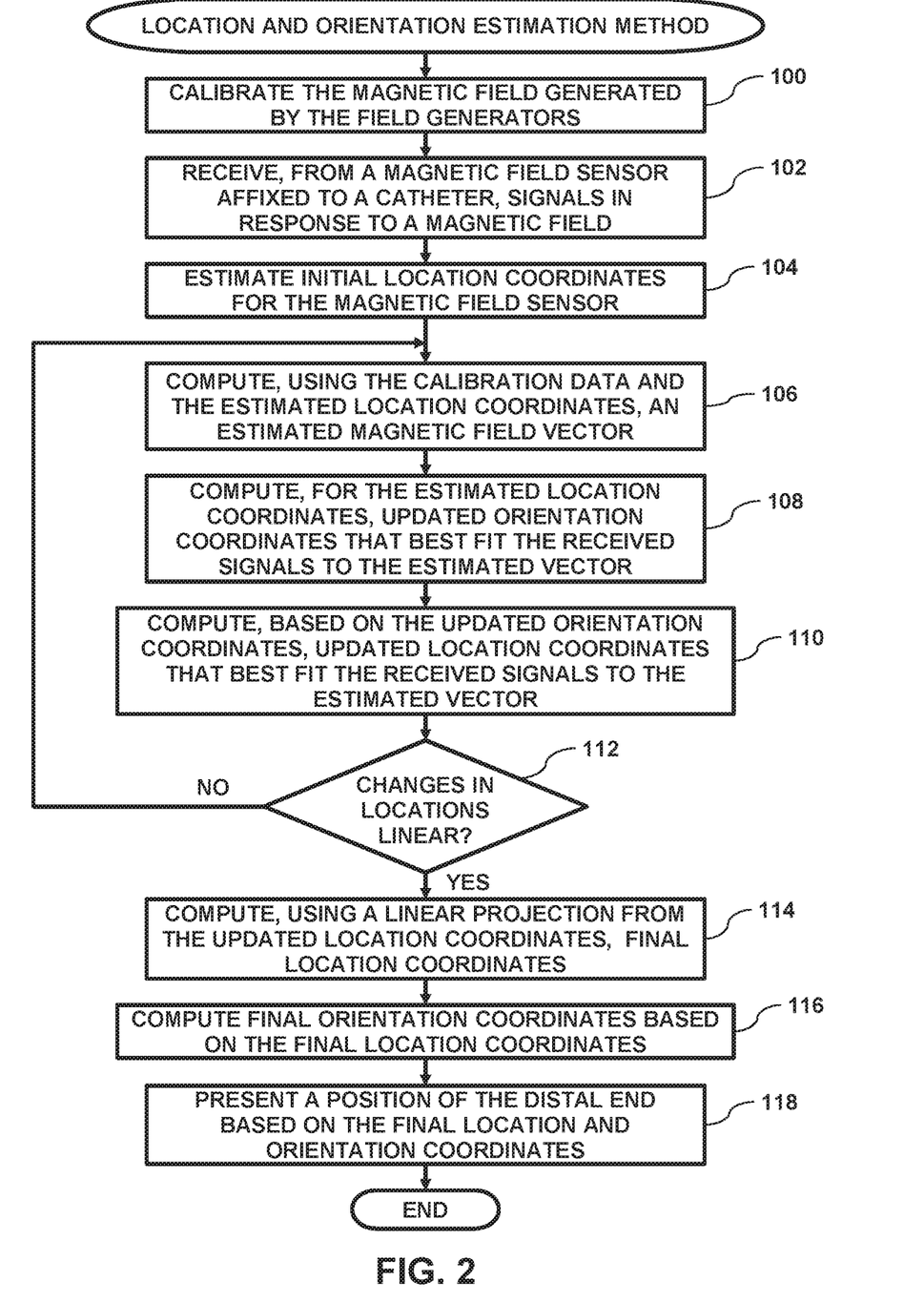
FIG. 2 is a flow diagram that schematically illustrates a method of performing iterations to estimate the location and the orientation of the distal end of the medical probe, in accordance with an embodiment of the present invention.
Figure 3:
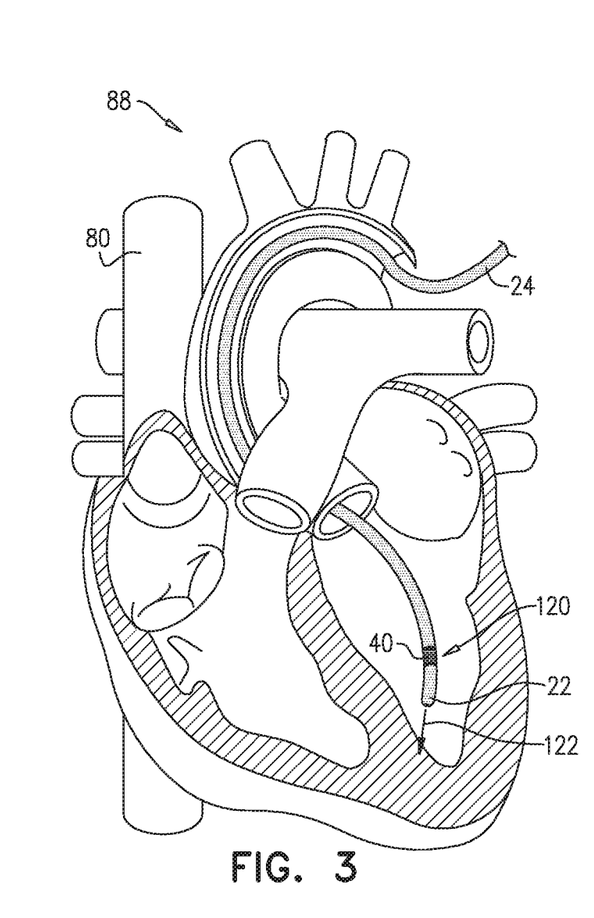
FIG. 3 is a schematic pictorial illustration of the distal end of the probe inside a chamber of a heart, in accordance with an embodiment of the present invention.

FIG. 2 is a flow diagram that schematically illustrates a method of estimating the location and orientation coordinates for distal end 22 of probe 24, and FIG. 3 is a schematic pictorial illustration of map 88, in accordance with an embodiment of the present invention. In a calibration step 100, processor 42 calibrates magnetic field generators 36, thereby calibrating magnetic fields 36.

To calibrate magnetic field generators 36, an individual places a magnetic field sensor (e.g., magnetic field sensor 40) at known locations in volume 30 (e.g., the center points of cubic regions 32) at a specific orientation. Upon positioning the magnetic sensor at each given location, processor 42 receives, from magnetic field sensor 40, signals in response to the magnetic field in the vicinity of the sensor, adds a new entry 56 to calibration table 50, and stores, in the new entry, coordinates of the given location to location coordinates 58 and values indicated by the signals to magnetic field measurements 60. In embodiments described herein the location coordinates and the magnetic field measurements stored in calibration table 50 may also be referred to as calibration data, and the signals are indicative of the respective magnetic fields at the known locations.

Upon starting a medical procedure, medical professional 84 manipulates probe 24 so that the distal end of the probe enters a chamber of heart 80 that is positioned within volume 30. In a receive step 102 processor 42 receives, from magnetic field sensor 40, sensor signals 48 in response to the calibrated magnetic fields in the vicinity of distal end 22. In an estimation step 104, processor 42 estimates, based on calibration table 50, location coordinates 54 of distal end 22. Therefore, the set of location coordinates selected by processor 42 are within working volume 30.

In a first computation step 106, processor 42 computes estimated magnetic field vector 52 based on the calibration data and the estimated location coordinates. To compute the magnetic field vector, processor 42 computes estimated signal measurements 76 based on an interpolation of the magnetic field measurements in the calibration table (i.e., based on the estimated location coordinates and the location coordinates in the calibration table).

In a second computation step 108, processor 42 computes, for estimated location coordinates 54, updated values for estimated orientation coordinates 78 that "best fit" the received sensor signals to estimated magnetic field vector 52. To compute the updated orientation coordinates, processor 42 can generate a first computed magnetic field based on the (current) estimated location and orientation coordinates, generate a second computed magnetic field that is based on the received signals, and then update estimated orientation coordinates 78 by "virtually rotating" the magnetic field sensor to find an orientation that best fits the first computed magnetic field to the second computed magnetic field.

In a third computation step 110, processor 42 computes, based on the updated orientation coordinates, updated values for location coordinates 54 that "best fit" the received sensor signals to estimated magnetic field vector 52. In a manner similar to the one described in step 108, processor 42 can generate, based on the calibration data, a first computed magnetic field based on the (current) estimated location and orientation coordinates, generate a second computed magnetic field that is based on the received signals, and then update estimated location coordinates 54 by "virtually moving" the magnetic field sensor to find a location that best fits the first computed magnetic field to the second computed magnetic field.

In a comparison step 112, if processor 42 detects changes in location coordinates 54 that do not meet a predefined linear criterion, then the method continues with step 106. In an embodiment of the present invention, the predefined linear criterion requires that the last three iterations of multiple iterations of steps 106-110 generate location coordinates that are linear in coordinate system 62.

In one embodiment, if the location coordinates (in x, y, or z) of the last three iterations are $a_1$, $a_2$, and $a_3$, then the location coordinates are linear if $(a_1-a_2)=(a_2-a_3)$ (i.e., within a specified threshold). In another embodiment, if $m(p_1, p_2)$ indicates a three-dimensional slope from location coordinates $p_1$ to location coordinates $p_2$, then coordinates $a_1$, $a_2$, and $a_3$ are linear if $m(a_1, a_2) \approx m(a_2, a_3)$ (i.e., within a specified threshold).

If in step 112, processor 42 detects that changes in location coordinates 54 meet the predefined linear criterion, then in a fourth computation step 114, the processor computes, using a linear projection from the currently updated estimated location coordinates, final location coordinates. In a manner similar to the description referencing step 110 hereinabove, processor 42 computes updated values for the final location coordinates by using the linear projection to "move" the estimated location coordinates to find new location coordinates 54 that processor 42 can use to compute a first magnetic field that "best fits" (i.e., most closely matches) a second magnetic field that the processor computes based on the received signals.

Figure 4:
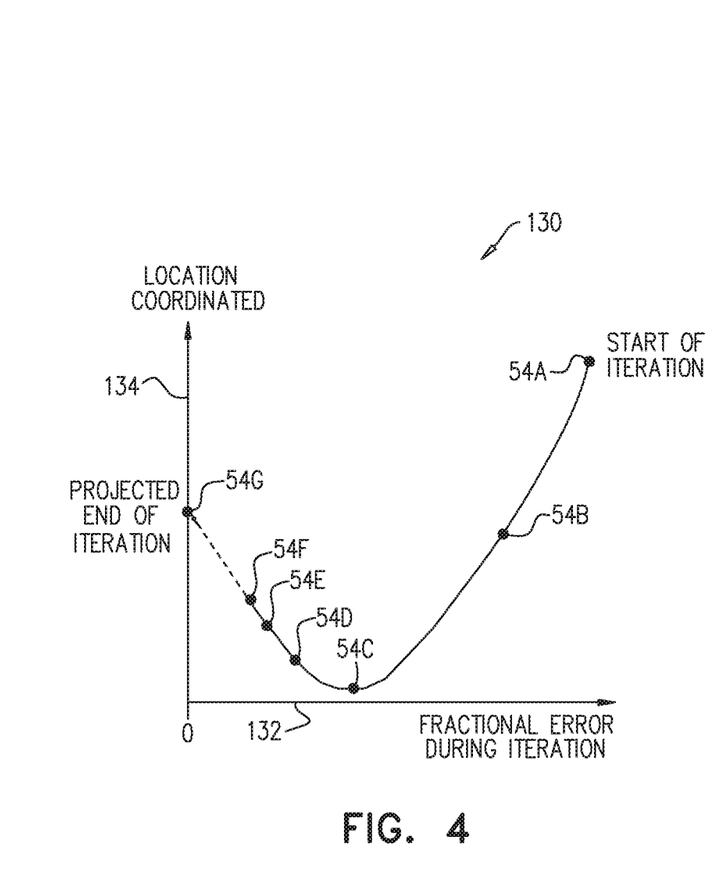
FIG. 4 is a schematic pictorial illustration of a chart that plots fixed location coordinates vs. fractional errors for location coordinates of the distal end that were computed during the iterations.

FIG. 4 is a schematic detail view of a chart 130 that plots fixed location coordinates 132 (i.e., in coordinate system 62) vs. fractional errors 134 for location coordinates 54 that processor 42 computed during successive iterations of steps 106-110 in FIG. 2. The fractional errors indicate differences between the first and the second computed magnetic fields as described supra. In one embodiment, processor 42 compute the fractional errors using the equation $$\text{Error} = \frac{\|B_{Observed} - B_{Estimated}\|}{\|B_{Observed}\|}$$

where Error is fractional error 134, $B_{Observed}$ is the second computed magnetic field described in the description referencing step 108 in FIG. 2 hereinabove, and $B_{Estimated}$ is the estimated magnetic field vector 52.

In FIG. 4, computed location coordinates 54 can be differentiated by appending a letter to the identifying numeral, so that the computed location coordinates comprise computed location coordinates 54-54G. As shown in the chart, upon processor 42 detecting linear changes in computed location coordinates 54D-54F, the processor can compute final location coordinates 54G by computing a linear projection from coordinates 54F to coordinates 54G, where the fractional error is as close to zero as possible.

Returning to the flow diagram, upon computing the final location coordinates, processor 42 computes final orientation coordinates, using the method described supra in steps 106 and 108. Finally, in a presentation step 118, and as shown in FIG. 3, processor 42 uses the final location and orientation coordinates to present, in map 88, distal end 22 at a location 120 and having an orientation 122, and the method ends.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising:

receiving by a processor, from a magnetic field sensor affixed to a probe, signals output by the sensor in response to a calibrated magnetic field in a vicinity of the probe;

estimating, by the processor, using calibration data of the calibrated magnetic field, location coordinates of the magnetic field sensor;

computing by the processor, using the calibration data and the estimated location coordinates, an estimated magnetic field vector comprising orientation coordinates;

computing by the processor, for the estimated location coordinates, updated orientation coordinates that fit the received signals to the estimated magnetic field vector;

computing by the processor, based on the updated orientation coordinates, updated location coordinates that fit the received signals to the estimated magnetic field vector;

repeating over multiple iterations the steps of computing the estimated magnetic field vector, computing the updated orientation coordinates, and computing the updated location coordinates and monitoring changes in the updated location coordinates over the iterations until the changes over a succession of the iterations meet a predefined linearity criterion;

upon detecting that the changes have met the linearity criterion, terminating the iterations and computing final location coordinates of the magnetic field sensor by a linear projection from the updated location coordinates; and presenting, on a display, a position of the probe based on the final location coordinates and the updated orientation coordinates, wherein the method comprises determining orientation of the distal end inside a predefined working volume, wherein the working volume comprises multiple cubic regions having uniform edge lengths, wherein the multiple iterations comprise a first iteration followed successively by a second iteration followed successively by a third iteration, and wherein the linearity criterion comprises detecting that a distance between the updated location coordinates computed during the first iteration and the updated location coordinates computed during the second iteration is in accordance with a distance between the updated location coordinates computed during the second iteration and the updated location coordinates computed during the third iteration, wherein the processor is adapted to identify fractional errors for location coordinates that the processor computed during successive iterations, wherein the fractional errors indicate differences between first and second computed magnetic fields, wherein the processor computes the fractional errors using the equation $$\text{Error} = \frac{\|B_{Observed} - B_{Estimated}\|}{\|B_{Observed}\|}$$

wherein Error is fractional error, $B_{Observed}$ is the second computed magnetic field and $B_{Estimated}$ is the estimated magnetic field vector.

2. The method according to claim 1, and comprising computing by the processor, using the calibration data and the final location coordinates, final magnetic field vector comprising orientation coordinates, computing by the processor, for the final location coordinates, final orientation coordinates that fit the received signals to the final magnetic field vector, and presenting, on the display, the position of the probe based on the final location coordinates and the final orientation coordinates.

3. The method according to claim 1, wherein the probe comprises an intracardiac catheter inserted into a chamber of a heart.

4. The method according to claim 1, wherein the orientation coordinates comprise Euler angles comprising a roll angle, a pitch angle and a yaw angle.

5. The method according to claim 1, wherein the location coordinates comprise three-dimensional coordinates on multiple axes in a coordinate system.

6. The method according to claim 1, wherein the multiple iterations comprise a first iteration followed successively by a second iteration followed successively by a third iteration, and wherein the linearity criterion comprises detecting that a slope from the updated location coordinates computed during the first iteration to the updates location coordinates computed during the second iteration is in accordance with a slope from the updated location coordinates computed during the second iteration to the updates location coordinates computed during the third iteration.

7. The method of claim 1 wherein the step of computing updated orientation coordinates comprises generating a first computed magnetic field based on the estimated location and orientation coordinates, generating a second computed magnetic field based on the received signals, and computing the updated estimated orientation coordinates by virtually rotating the magnetic field sensor to find an orientation that fits the first computed magnetic field to the second computed magnetic field.

8. The method of claim 1 wherein the step of computing updated location coordinates comprises generating, based on the calibration data, a first computed magnetic field based on the estimated location and orientation coordinates, generating a second computed magnetic field that is based on the received signals, and computing the update location coordinates by virtually moving the magnetic field sensor to find a location that fits the first computed magnetic field to the second computed magnetic field.

9. An apparatus, comprising:

a medical probe configured to be inserted into a body cavity;

a magnetic field sensor affixed to the probe; a display; and a processor configured:

to receive, from the magnetic field sensor affixed to the probe, signals output by the sensor in response to a calibrated magnetic field in a vicinity of the probe, to estimate, using calibration data of the calibrated magnetic field, location coordinates of the magnetic field sensor, to compute, using the calibration data and the estimated location coordinates, an estimated magnetic field vector comprising orientation coordinates, to compute, for the estimated location coordinates, updated orientation coordinates that fit the received signals to the estimated magnetic field vector, to compute, based on the updated orientation coordinates, updated location coordinates that fit the received signals to the estimated magnetic field vector, to repeat over multiple iterations the steps of computing the estimated magnetic field vector, computing the updated orientation coordinates, and computing the updated location coordinates and monitoring changes in the updated location coordinates over the iterations until the changes over a succession of the iterations meet a predefined linearity criterion, upon detecting that the changes have met the linearity criterion, to terminate the iterations and to compute final location coordinates of the magnetic field sensor by a linear projection from the updated location coordinates, and to present, on the display, a position of the probe based on the final location coordinates and the updated orientation coordinates, wherein the processor is adapted to determine orientation of the probe inside a predefined working volume, wherein the working volume comprises multiple cubic regions having uniform edge lengths, wherein the multiple iterations comprise a first iteration followed successively by a second iteration followed successively by a third iteration, and wherein the linearity criterion comprises detecting that a distance between the updated location coordinates computed during the first iteration and the updated location coordinates computed during the second iteration is in accordance with a distance between the updated location coordinates computed during the second iteration and the updated location coordinates computed during the third iteration, wherein the processor is adapted to identify fractional errors for location coordinates that the processor computed during successive iterations, wherein the fractional errors indicate differences between first and second computed magnetic fields, wherein the processor computes the fractional errors using the equation $$\text{Error} = \frac{\|B_{Observed} - B_{Estimated}\|}{\|B_{Observed}\|}$$

wherein Error is fractional error, $B_{Observed}$ is the second computed magnetic field and $B_{Estimated}$ is the estimated magnetic field vector.

10. The apparatus according to claim 9, wherein the processor is configured to compute, using the calibration data and the final location coordinates, final magnetic field vector comprising orientation coordinates, to compute, for the final location coordinates, final orientation coordinates that fit the received signals to the final magnetic field vector, and to present, on the display, the position of the probe based on the final location coordinates and the final orientation coordinates.

11. The apparatus according to claim 9, wherein the probe comprises an intracardiac catheter inserted into a chamber of a heart.

12. The apparatus according to claim 9, wherein the orientation coordinates comprise Euler angles comprising a roll angle, a pitch angle and a yaw angle.

13. The apparatus according to claim 9, wherein the location coordinates comprise three-dimensional coordinates on multiple axes in a coordinate system.

14. The apparatus according to claim 9, wherein the multiple iterations comprise a first iteration followed successively by a second iteration followed successively by a third iteration, and wherein the linearity criterion comprises detecting that a slope from the updated location coordinates computed during the first iteration to the updates location coordinates computed during the second iteration is in accordance with a slope from the updated location coordinates computed during the second iteration to the updates location coordinates computed during the third iteration.

15. The system of claim 9 wherein computing updated orientation coordinates comprises generating a first computed magnetic field based on the estimated location and orientation coordinates, generating a second computed magnetic field based on the received signals, and computing the updated estimated orientation coordinates by virtually rotating the magnetic field sensor to find an orientation that fits the first computed magnetic field to the second computed magnetic field.

16. The system of claim 9 wherein computing updated location coordinates comprises generating, based on the calibration data, a first computed magnetic field based on the estimated location and orientation coordinates, generating a second computed magnetic field that is based on the received signals, and computing the update location coordinates by virtually moving the magnetic field sensor to find a location that fits the first computed magnetic field to the second computed magnetic field.

17. A computer software product, operated in conjunction with a probe that is configured for insertion into a body cavity of a patient and includes a magnetic sensor, the product comprising a non-transitory computer-readable medium, in which program instructions are stored, which instructions, when read by a computer, cause the computer:

to receive, from the magnetic field sensor affixed to the probe, signals output by the sensor in response to a calibrated magnetic field in a vicinity of the probe;

to estimate, using calibration data of the calibrated magnetic field, location coordinates of the magnetic field sensor;

to compute, using the calibration data and the estimated location coordinates, an estimated magnetic field vector comprising orientation coordinates;

to compute, for the estimated location coordinates, updated orientation coordinates that fit the received signals to the estimated magnetic field vector; to compute, based on the updated orientation coordinates, updated location coordinates that fit the received signals to the estimated magnetic field vector;

to repeat over multiple iterations the steps of computing the estimated magnetic field vector, computing the updated orientation coordinates, and computing the updated location coordinates and monitoring changes in the updated location coordinates over the iterations until the changes over a succession of the iterations meet a predefined linearity criterion;

upon detecting that the changes have met the linearity criterion, to terminate the iterations and to compute final location coordinates of the magnetic field sensor by a linear projection from the updated location coordinates; and to present, on a display, a position of the probe based on the final location coordinates and the updated orientation coordinates, wherein the software is adapted to determine orientation of the probe inside a predefined working volume, wherein the working volume comprises multiple cubic regions having uniform edge lengths, wherein the multiple iterations comprise a first iteration followed successively by a second iteration followed successively by a third iteration, and wherein the linearity criterion comprises detecting that a distance between the updated location coordinates computed during the first iteration and the updated location coordinates computed during the second iteration is in accordance with a distance between the updated location coordinates computed during the second iteration and the updated location coordinates computed during the third iteration, wherein the software is adapted to identify fractional errors for location coordinates that the processor computed during successive iterations, wherein the fractional errors indicate differences between first and second computed magnetic fields, wherein the processor computes the fractional errors using the equation $$\text{Error} = \frac{\|B_{Observed} - B_{Estimated}\|}{\|B_{Observed}\|}$$

wherein Error is fractional error, $B_{Observed}$ is the second computed magnetic field and $B_{Estimated}$ is the estimated magnetic field vector.

* * * * *